US006833250B2

(12) United States Patent
Potts et al.

(10) Patent No.: US 6,833,250 B2
(45) Date of Patent: Dec. 21, 2004

(54) DETECTION AND REMOVAL OF CHITINOUS MATERIAL IN A BIOLOGICAL SAMPLE

(75) Inventors: Steven J. Potts, Davis, CA (US); David C. Slaughter, Davis, CA (US); James F. Thompson, Sacramento, CA (US); Jennifer J. Payne, Davis, CA (US); Barb Ariel Cohen, Watertown, MA (US)

(73) Assignee: Vicam, L.P., Watertown, MA (US)

( * ) Notice: Subject to any disclaimer, the term of this patent is extended or adjusted under 35 U.S.C. 154(b) by 79 days.

(21) Appl. No.: 09/759,815

(22) Filed: Jan. 10, 2001

(65) Prior Publication Data

US 2002/0107179 A1 Aug. 8, 2002

Related U.S. Application Data

(63) Continuation-in-part of application No. 09/519,533, filed on Mar. 6, 2000.

(51) Int. Cl.$^7$ ................................................. C12Q 1/04
(52) U.S. Cl. .......................................... 435/34; 435/18
(58) Field of Search ..................... 435/34, 18; 436/827; 530/370

(56) References Cited

U.S. PATENT DOCUMENTS

| 4,289,747 A | 9/1981 | Chu |
| 4,493,793 A | 1/1985 | Chu |
| 4,526,871 A | 7/1985 | Avrameas et al. |
| 4,659,658 A | 4/1987 | McCarthy et al. |
| 5,250,410 A | 10/1993 | Slifkin |
| 5,587,292 A | 12/1996 | Laine |
| 5,914,239 A | 6/1999 | Laine |
| 6,121,420 A | 9/2000 | Laine |

OTHER PUBLICATIONS

Gourama H. Detection of Molds in Foods and Feeds. J of Food Protection 58(12)1389–1394 1995.*
Cousin M. Chitin as a Measure of Mold Contamination of Agricultural Commodities and Foods. J of Food Protection 59(1)73–81, 1995.*
Potts S. A Fluorescent Lectin Test for Mold in Raw Tomato Juice. J of Food Science 65(2)346–350 2000.*
Baldo B. Lectins as Cytochemical Probes of the Developing Wheat Grain. Australian J Plant Physiol 9 663–75, 1982.*
Cousin (1996) "Chitin as a Measure of Mold Contamination of Agricultural Commodities and Foods." *J. Food Protection*, 59:73–81.
Gourama and Bullerman (1995) "Detection of Molds in Foods and Feeds: Potential Rapid and Selective Methods." *J. Food Protection*, 58:11389–1394.
Jarvis (1977) "A chemical method for the estimation of mould in tomato products." *J. Food Technology*, 12:581–591.
Jarvis and Williams (1987) "Method for Detecting Fungi in Foods and Beverages." *Food and Beverage Mycology*, 2$^{nd}$ ed., Editor L.R. Beuchat, Van Nostrand Reinhold, New York, pp. 599–636.
Jarvis et al., (1983) "Observations on the enumeration on moulds in food and feedingstuffs" *J. Appl. Bacteriol.* 55:325–336.
Lin & Cousin (1985) "Detection of Mold in Processed Foods by High Performance Liquid Chromatography." *J. Food Protection*, 48:671–678.
Lis & Sharon (1986) "Lectins as Molecules and as Tools." *Ann. Rev. Biochem.*, 55:35–67.
Patel (1992) "The applications of lectins in food analysis." *Trends in Food Sci. & Technol.* 3:35–39.
Patel et al., (1993) "Rapid Separation and Detection of Foodborne Yeasts and Moulds by Means of Lectins." In *New Techniques in Food and Beverage Microbiology*, pp. 31–41, Knoll, R.G., Gilmour, A., and Sussman, M., Eds. Blackwell Science Inc. Oxford, England.
Ride and Drysdale (1972) "A rapid method for the chemical estimation of filamentous fungi in plant tissue." *Physiol. Plant Pathol.* 2:7–15.
Stoddart and Herbertson (1978) "The Use of Fluorescein–labeled Lectins in the Detection and Identification of Fungi Pathogenic for Man: A Preliminary Study." *J. Med. Microbiol.* 11:315–324.
Battilani et al. (1996) "Fungal Growth and Ergosterol Content in Tomato Fruits Infected to Fungi." *Ital. J. Food Science* 4:283–289.
Eisenburg (1952) "Observations and Suggestions on Factory Control of Rot and Extreneous Matter in Tomato Products." *Nat. Can Assoc., Inc.* Let No. 1371.
Howard (1911) "Tomato Ketchup Under the Microscope: With Practical Suggestions to Insure a Cleanly Product." *U.S. Dept. Agr. Bureau of Chemistry*, Circular No. 68.
Sharma, P.D. et al. (1977) "Critique of the Chitin Assay Technique for Estimation of Fungal Biomas." *Trans. Br. Mycol. Soc.* 69:479–483.
Williams (1968) "The Detection of Rot in Tomato Products." *J. Ass. Pub. Analysts*, 6:69–84.
Potts et al. (2000) "A Fluorescent Lectin Test for Mold in Raw Tomato Juice." *Journal of Food Science*, vol. 65, No. 2: 346–350.

* cited by examiner

*Primary Examiner*—Ralph Gitomer
(74) *Attorney, Agent, or Firm*—Wolf, Greenfield & Sacks, P.C.

(57) ABSTRACT

This invention provides novel methods for the detection of chitinous contaminants of non-chitinous biological materials. The methods are accurate, highly reproducible, rapid and relatively inexpensive. The methods are well suited to commercial applications, particularly in the food and agriculture industry where biological materials (e.g. food products) are regularly screened for contaminants (e.g. insect, mold, fungus, etc.). In one embodiment, the methods involve contacting a biological sample with a probe that is a lectin that binds chitin, contacting the sample with a pectinase; and detecting binding of said lectin to a chitin where the binding indicates the presence of chitin in the biological sample.

46 Claims, 7 Drawing Sheets

DETECTION AND REMOVAL OF CHITINOUS MATERIAL IN A BIOLOGICAL SAMPLE

CROSS-REFERENCE TO RELATED APPLICATIONS

This is a continuation-in-part of U.S. Ser. No. 09/519,533, filed on Mar. 6, 2000 which is incorporated herein by reference in its entirety for all purposes.

STATEMENT AS TO RIGHTS TO INVENTIONS MADE UNDER FEDERALLY SPONSORED RESEARCH AND DEVELOPMENT

[ Not Applicable ]

FIELD OF THE INVENTION

This invention relates to the field of microorganism detection. In particular, this invention provides an improved methodology for detecting chitinous contaminants in samples, e.g. biological samples.

BACKGROUND OF THE INVENTION

A methodology for rapid detection and identification of microorganisms, and other contaminants, has long been a concern to the medical, pharmaceutical and food processing fields, among others. Because of this sustained interest, significant advances over the classical time consuming methods of plate counting, membrane filtration, or multiple tube fermentation procedures have been noted. Such approaches include, differential dye-cell wall binding, mass spectrometry, bacteriophage lysis, computer assisted probability methods, gel ferrography, flow cytometry, and the like. Such methods, however, typically have not achieved industry acceptance particularly in the agricultural and food industry. This lack of acceptance/industry implementation is due to disadvantages such as laborious and time-consuming laboratory preparation and sample handling, long observation times and nonspecificity with respect to microorganism characterization and subsequent identification, and increased expense in terms of labor and/or instrumentation. Thus, relatively primitive methods are employed for monitoring contaminants, e.g. in agricultural products.

Thus, for example, California tomato industry monitors mold levels in raw product at inspection stations and in processed product in quality control laboratories. At the inspection stations, 23 kg of fruit from each 24 metric ton truckload of processing tomatoes are visually inspected for defects. Tomatoes with visible signs of mold are weighed to obtain a percentage of decayed fruit on a mass basis (PTAB, 1996). At the processor's quality control laboratories, mold is quantified by the Howard mold count (HMC) method (AOAC, 1984), where a small drop of homogenized juice is inspected using a microscope. In the HMC method, two slides of twenty-five fields each are viewed, and the percentage of fields containing mold are recorded. An accurate HMC takes up to thirty minutes to conduct.

Over the last several decades, many attempts have been made to replace manual grading and the Howard mold count with a less subjective and less labor-intensive measurement, but no method has been accurate, rapid, and simple enough to use at inspection stations or in quality control laboratories (Jarvis and Williams (1987). p. 599–636. In *Food and Beverage Mycology*, ed. L. R. Beuchat, $2^{nd}$ ed. Van Nostrand Reinhold, N.Y.; Gourama and Bullerman (1995) *Journal of Food Protection* 58:1389–1394; and Cousin (1996) *Journal of Food Protection*, 59: 73–81). Despite the difficulties and limitations of the HMC (e.g. Williams (1968) *J. Ass. Pub. Analysts*, 6: 69–84; Jarvis et al. (1983) *J. Appl. Bacteriol.* 55: 325), it remains the universal standard for mold assessment almost ninety years after it was first introduced (Howard (1911) *U.S. Dept. Agr., Bureau of Chemistry, Circular No. 68*).

Chitin is an important structural component in fungal cell walls, but absent from plant tissue. The detection of mold based on the chemical isolation and quantification of N-acetyl-D-glucosamine, a breakdown product of chitin, has been proposed as an alternative mold measurement (Ride and Drysdale (1972) *Physiol. Plant. Pathol.* 2: 7–15; Jarvis (1977) *J. Food Technol.* 12: 581–591; Lin and Cousin (1985) *Journal of Food Protection*, 59: 73–81). Jarvis (1977), supra., found a coefficient of variation (CV) of around 20% for this method. Although the high performance liquid chromatography based isolation method is too slow and labor intensive to be utilized as an industrial replacement for the HMC, a more rapid method that detects chitin could have commercial promise (Cousin (1996) *Journal of Food Protection*, 59: 73–81).

Lectins are naturally occurring proteins or glycoproteins that bind to specific carbohydrates. They are becoming increasingly valuable as molecular probes, including the labeling of cell-surface components in tissue typing (Lis and Sharon (1986) *Ann. Rev. Biochem.* 55: 35–67). Hundreds of lectins from microbial, plant, and animal cells have been identified, but most commercially available lectins are isolated from plant seeds. They are available with various enzymatic and fluorescent labels, and their nomenclature derives from the name of their source.

There are numerous commercially available lectins that bind polymers of N-acetyl-D-glucosamine. Stoddard and Herbertson (1978) *J. Med. Microbiol.* 11: 315–324, utilized fluorescein labeled lectins to detect human pathogenic fungi. Patel (1992) The applications of lectins in food analysis. *Trends in Food Sci. & Technol.* 3: 35–39, used fluorescein isothiocyanate (FITC) labeled lectins to observe mold in processed foods. He tested several chitin-binding lectins, and found that a lectin from wheat germ agglutinin (WGA) had the strongest binding to fungal cell walls and the least amount of nonspecific binding to tomato cells. He observed considerable autofluorescent signal, tomato cell tissue that fluoresces at similar wavelengths as the fluorescent probe. Patel et al. (1993) pages 31–41 In *New Techniques in Food and Beverage Microbiology* Eds. Kroll, R. G., Gilmour, A., and Sussman, M. Blackwell Science Inc. Oxford, England, used biotinylated lectins and streptavidin labeled magnetic particles to separate and concentrate mold spores and yeasts in fruit juices.

SUMMARY OF THE INVENTION

This invention provides novel methods for the detection of chitinous contaminants of non-chitinous biological materials. The methods are accurate, highly reproducible, rapid and relatively inexpensive. The methods are well suited to commercial applications, particular in the food and agriculture industry where biological materials (e.g. food products) are regularly screened for contaminants (e.g. insect, mold, fungus, etc.).

In one embodiment this invention provides a method of detecting chitinous material in a processed non-chitinous biological sample. The method involves contacting the biological sample with a probe that is a lectin that binds chitin, contacting the biological sample with a pectinase, and detecting binding of the lectin to a chitin wherein the binding indicates the presence of chitin (and hence a chitinous contaminant) in the biological sample. The chitinous contaminant can be any of a wide variety of contaminants including, but not limited to insects, insect parts, other animals or parts of animals of the phylum arthropoda (e.g. crustacea), nematodes, annelids, molds, fungi, slimes, yeasts, and various other microorganisms, and the like. In particularly preferred embodiments, the detected contaminant is a fungus of phylum Ascomycota, Basidomycota, Chytridiomycota, or Zygomycota, or a member of the phylum Oomycota in the Stramenopila kingdom. Particularly preferred fungi include, but are not limited to Cladosporium spp, Fusarium spp, Stemphylium spp, Alternaria spp, Geotrichum spp, Fusarium spp, Rhizopus spp, Botrytis spp, Phytophthora spp, Pythium spp, or Pythium spp (e.g. *Cladosporium herbarum, Fusarium oxysporum*, and *Stemphylium botryosum, Alternaria alternata, Geotrichum candidum, Fusarium oxysporum, Rhizopus stolonifer, Botrytis cinerea, Phytophthora parasitica, Pythium aphanidermatum, Pythium ultimum*, etc.).

Preferred biological samples include, but are not limited to an agricultural product, a food product, a wood product, a textile, and an animal tissue product. Particularly preferred agricultural products include, but are not limited to fruits, vegetables, grains, forages, silages, juices (vegetable or fruit), a wood, flowers, or seeds. In one embodiment the agricultural product is a tomato, a pepper, a grape, an apple, an orange, a lemon, a berry, or a juice or concentrate thereof.

Preferred lectins for use in this invention include, but are not limited to wheat germ agglutenin (WGA), succinylated WGA, pokeweed lectin, tomato lectin, potato lectin barley lectin, rice lectin, stinging nettle lectin, a vicilin, a chitovibrin, a Vibrio lectin, and a hevein. The lectin is preferably a lectin labeled with a detectable label (e.g., a radioactive label, a magnetic label, a colorimetric label, an enzymatic label, a fluorescent label, a metal, an antibody, a biotin, an avidin, or streptavidin). Fluorescent labels are most preferred. Where fluorescent labels are used, the detecting preferably involves using a fluorometer to detect fluorescence of the label. In particularly preferred embodiments the fluorometer uses a bandpass filter. While virtually any fluorometer is suitable in a most preferred embodiment, the fluorometer is a surface-reading fluorometer.

In certain embodiments, the method is performed at a basic pH greater than about pH 7 (e.g. at about pH 8).

Preferred pectinases for use in the methods of this invention include, but are not limited to polygalacturonases, pectinesterases, pectin lyases, and hemicellulases. The methods of this invention also, optionally, involve using a blocking agent to reduce non-specific binding of the lectin. Blocking agents are well known to those of skill in the art. One preferred blocking agent is serum albumin (e.g. bovine serum albumin).

Preferred processed biological samples include samples that have been subjected to an operation selected from the group consisting of comminuting, homogenizing, heating, evaporation, lyophylization, filtering, concentrating, filtering, fermenting, freezing, and blanching.

In certain embodiments, the biological sample is selected from the group consisting of a fruit, a vegetable, a fruit juice, and a vegetable juice, the lectin is a fluorescently labeled lectin selected from the group consisting of wheat germ agglutenin (WGA), succinylated WGA, pokeweed lectin, tomato lectin, potato lectin barley lectin, rice lectin, stinging nettle lectin, a vicilin, a chitovibrin, a Vibrio lectin, and a hevein, the pectinase is a pectinase selected from the group consisting of polygalacturonases, pectinesterases, pectin lyases and hemicellulases, the sample is processed by comminuting, homogenizing, heating, evaporation, lyophylization, filtering, concentrating, filtering, fermenting, freezing, and blanching; and the detecting comprises detecting a signal from the fluorescent label labeling said lectin.

In another embodiment, this invention provides methods of detecting chitinous material in a non-chitinous biological sample. These methods involve contacting the biological sample with a fluorescently labeled probe that is a lectin that binds chitin, where the contacting is in a solution at a pH ranging from about pH 7 to about pH 9, contacting said biological sample with a fluorescently labeled probe that is a lectin that binds chitin; and detecting binding of the lectin to a chitin wherein said binding indicates the presence of chitin in said biological sample. Preferred contaminants, biological samples, and lectins include one or more of the biological samples, lectins, and contaminants described above. Preferred detection methods utilize a fluorometer (e.g. a surface-reading fluorometer) to detect fluorescence of said label. The fluorometer is optionally equipped with a bandpass filter. The assay is preferably performed at a pH greater than about pH 7.5, more preferably at a pH about pH 8.0. In one preferred embodiment, the biological sample is a fruit, a vegetable, a fruit juice, or a vegetable juice, the lectin is a fluorescently labeled lectin selected from the group consisting of wheat germ agglutenin (WGA), succinylated WGA, pokeweed lectin, tomato lectin, potato lectin, barley lectin, rice lectin, stinging nettle lectin, a vicilin, a chitovibrin, a Vibrio lectin, and a hevein, and the detecting comprises detecting a signal from the fluorescent label labeling said lectin. The method may optionally further involve contacting the biological sample with a pectinase (e.g., a polygalacturonase, a pectinesterase, a pectin lyase a hemicellulase, etc.).

In another embodiment this invention provides a biological sample in which a lectin that specifically binds to chitin is bound to a chitinous contaminant of the sample, and the lectin is labeled with a label that provides a signal distinguishable from a background signal where the signal indicates the presence or quantity of the chintinous contaminant in the biological sample. Such a biological sample may occur in an assay of this invention or may be utilized as a positive control. In preferred embodiments ,the pH of the sample is basic ranging from about pH 7 to about pH 9. Preferred samples are processed samples e.g., as described herein. The sample may, optionally, further comprise an exogenously supplied pectinase. Preferred lectins and/or pectinases include, but are not limited to lectins and/or pectinases as described herein.

In still another embodiment, this invention provides a kit for detecting chitinous material in a non-chitinous biological sample. Preferred kits include a first container containing a lectin that specifically binds a chitinous material, and a second container containing a pectinase. In certain embodiments, the first container and second containers are the same container. Pectinases and/or lectins include, but are not limited to the pectinases and/or the lectins described herein. Certain kits can, optionally, further comprise a label for labeling the lectin, while in certain other embodiments, the lectin is already labeled. The kit can optionally further comprise a transparent centrifugable receptacle (e.g. a flow-through centrifuge) suitable for use with a surface-reading fluorometer and/or a bandpass filter for that passes light emitted by a fluorescent label in the kit.

In yet another embodiment, this invention. provides methods of detecting a fluorochrome bound to one phase of a two-phase mixture. These methods involve contacting a transparent surface of a receptacle with a solid or semi-solid phase of the two phase mixture, illuminating the solid or semisolid phase of the two phase mixture through the transparent surface, and detecting through the transparent surface fluorochrome bound to the solid or semi-solid phase of said two-phase mixture. The receptacle is preferably a centrifuge tube (e.g. or a flow-through centrifuge). The contacting can comprise spinning the receptacle so that the solid or semi-solid phase is deposited against the transparent surface. In preferred embodiments, the two-phase mixture comprises a biological sample (e.g. as described above), with preferred two-phase mixtures including, but not being limited to, fruit and/or vegetable juices, homogenates, or concentrates). The fluorochrome is preferably a chitin-specific fluorescently labeled lectin as described herein.

This invention also provides a surface-reading fluorometer comprising a receptacle having a transparent surface, the receptacle being compatible with centrifugation in a centrifuge; a light source for illuminating a sample through the transparent surface; and a detector disposed to detect fluorescence through the transparent surface.

DEFINITIONS

The terms "chitinous material" refers to a material comprising chitin and/or a breakdown product of chitin (e.g. N-acetyl-D-glucosamine). Chitin includes regenerated chitin (fully acetylated chitin) and chitosan (deacetylated chitin).

The term "lectins" refers to carbohydrate-binding proteins or glycoproteins of non-immune origin that agglutinate cells or that precipitate glycoconjugates, or are simply carbohydrate-binding proteins of non-immune origin. Lectins have been isolated from a wide variety of organisms, including bacteria, invertebrates, vertebrates, and plants. Lectins are often glycosylated, and are frequently composed of homo- or heterodimers with one binding site per subunit.

The term "specifically binds", when referring to the interaction of a lectin probe and its chitin target refer to a binding reaction that is determinative of the presence of the chitin (or chitin degradation product) in a heterogeneous population of molecules (e.g., proteins and other biologics). Thus, for example, in the case of a lectin of this invention, the lectin preferentially (or specifically) binds to chitin (or chitin degradation product) when the chitin-lectin complex can be distinguished from interactions between the lectin and the non-chitinous biological sample. In general, a signal to noise ratio of 1.2 or greater preferably 1.5 or greater, more preferably 2 or greater, and most preferably 3 or greater (where the signal to noise is the ratio of chitin-specific signal to background signal) indicates detection of a specific binding.

A "processed sample" or a "processed biological sample" refers to a sample of a biological material subjected to one or more processes typically used in the commercial preparation of the biological material. Processing often involves one or more forms of preservation, and/or disinfection, and/or fractionation, and/or homogenization or other "lytic" process. Thus, for example, processing may involve extraction of a juice from a fruit or a vegetable and/or pasteurization of that juice. Other "processing" operations are well known to those of skill in the art and include, but are not limited to addition of preservatives, exposure to radiation, lyophilization, crystallization, dehydration, comminution, heating (e.g. pasturization), evaporation, lyophylization, filtration, concentration, fermentation, freezing, and blanching.

A "non-chitinous biological sample" refers to a biological sample taken from an organism, an organ, and/or a tissue, and/or a cell or cell culture in which chitin does not typically exist. Examples of "non-chitinous biological samples" include, but are not limited to samples of higher plants (e.g. fruits) or products derived therefrom (e.g. juices, juice concentrates, homogenates, etc.) samples from vertebrates, and the like.

Pectinases are well known enzymes that characteristically break down pectins (polysaccharides typically found in plant cell walls). The term "pectinases" is intended to include polygalacturonases (EC3.2.1.15), pectinesterases (EC3.2.1.11), pectin lyases (EC4.2.2.10) and hemicellulases such as endo-1,3-β-xylosidase (EC 3.2.1.32), xylan 1,4-β-xylosidase (EC 3.2.1.37), α-L-arabinofuranosidase (EC 3.2.1.55), and the like.

A "microorganism" generally refers to a living organism too small to be seen with the naked eye. Microorganisms include, but are not limited to bacteria, fungi, protozoans, microscopic algae, and viruses.

"Agricultural product(s)", as used herein, refers to plants and/or plant parts, more preferably commercially relevant plants and/or plant parts. Such plants and/or plant parts include, but are not limited to plant vegetative organs (e.g. leaves, roots, stems, and tubers), flowers and floral organs (e.g. bracts, sepals, petals, stamens, carpels, anthers and ovules), wood and cellulose-based products, seed (including embryo, endosperm, and seed coat), and fruit (the mature ovary), e.g. the harvested product of numerous agronomically-important crop plants. Agricultural products also include processed agricultural products (e.g. dried fruits and/or vegetables, fruit and/or vegetable homogenates and/or concentrates, and/or juices, textiles or cotton products, wood products, etc.) Preferred crop plants include, but are not limited to tomatoes, citrus fruits, pears, apples, peaches, corn, oats, wheat, rice, soybean, alfalfa, barley, millet, hops, as well as numerous grains and/or forages.

DETAILED DESCRIPTION

Figure 1:
FIG. 1 illustrates an infected tomato fruit showing growth of *Fusarium oxysporum*.

The invention provides a rapid and inexpensive method of quantifying chitinous contaminants in non-chitinous samples, e.g. samples of biological materials. A wide variety of contaminants, particularly of food stuffs, are of importance to the public health. As a consequence numerous health regulations exist mandating the screening of raw and/or processed foods and/or agricultural products.

Of the potential contaminants of biological samples (e.g. food/agricultural products) a great many are themselves biological in nature. Of these biological contaminants, many are chitinous (e.g. contain some form of chitin). In particular, a large variety of microorganisms including, but not limited to bacteria, mold, fungi, and the like and various invertebrates (e.g. insects, mites, etc.) incorporate various forma of chitin.

In contrast, a wide variety of biological materials, notably vertebrate tissues, plants, and the like do not contain chitin. Thus, chitin provides a good target for detecting a large number of contaminants. Prior to this invention, however, measurements of contaminants exploiting chitin or chitin products, as a marker, or target, have been expensive, and/or labor intensive, and/or of poor reliability.

This invention provides inexpensive, rapid methods of detecting chitin (e.g. chitin-containing organisms) in non-chitinous samples. The methods show unusually high reliability and reproducibility, and are well suited to mass screening, e.g. in a commercial context. In general, the methods utilize a labeled lectin to specifically bind to the chitin and the label on the lectin is detected and/or quantified providing a measurement of the chitinous contamination in the sample.

The biological sample can include any biological material in which it is desired to detect and/or quantify the presence of a chitinous contaminant. Preferred biological samples include, but are not limited to, samples of animal tissues and/or agricultural products. Preferred samples of animal tissues include, but are not limited to samples of raw meat, or meat products and/or processed meats and/or meat products. Agricultural products, as used herein, refers to plants and/or plant parts, more preferably commercially relevant plants and/or plant parts. Such plants and/or plant parts include, but are not limited to plant vegetative organs (e.g. leaves, roots, stems, and tubers), flowers and floral organs (e.g. bracts, sepals, petals, stamens, carpels, anthers and ovules), seed (including embryo, endosperm, and seed coat), wood and cellulose based products, and fruit (the mature ovary), e.g. the harvested product of numerous agronomically-important crop plants. Agricultural products also include processed agricultural products (e.g. dried fruits and/or vegetables, fruit and/or vegetable homogenates and/or juices, textiles or cotton products, wood products, etc.) Preferred crop plants include, but are not limited to tomatoes, citrus fruits, pears, apples, peaches, corn, oats, wheat, rice, soybean, alfalfa, barley, millet, hops, as well as numerous grains and/or forages. Methods of obtaining such biological samples are well known to those of skill in the art.

Particularly in the case of agricultural products, the assays are designed to detect contaminants comprising various fungi (e.g. *Cladosporium herbarum, Fusarium oxysporum, and Stemphylium botryosum, Alternaria alternata, Geotrichum candidum, Fusarium oxysporum, Rhizopus stolonifer, Botrytis cinerea*, etc.), various slimes and moulds (e.g. Black mold, Gray mold, White mold, Brown mold, Blue mold, Green mold, etc.), yeasts, and various insects and/or insect parts in raw and/or processed products. It was a surprising discovery that organisms in the kingdom Straminopila, phylum Oomycota, (e.g., *Phytophthora parasitica, Pythium aphanidermatum*, and *Pythium ultimum*) were detected using the chitin specific lectin. These organisms are not "true fungi" and are not considered to have high levels of chitin in their cell walls. Pythium spp. causes water rot in tomatoes, while Pythophthora spp. causes late blight and buckeye rot.

Detection of Contaminants in "Processed" Samples.

In one embodiment, the methods of this invention are particularly well suited to applications involving detecting of contaminants in processed biological materials. The methods typically involve contacting the biological sample with a probe (preferably labeled) that is a lectin that binds chitin; contacting the biological sample with a pectinase (or in certain embodiments a blocking agent such as serum albumin, e.g. BSA); and detecting binding of the lectin to a chitin where the binding indicates the presence of chitin in said biological sample.

The term "processed" when used in reference to processed biological materials, refers to a process typically used in the commercial preparation of the biological material. Processing often involves one or more forms of preservation, and/or disinfection, and/or fractionation, and/or homogenization or other "lytic" process. Thus, for example, processing may involve extraction of a juice from a fruit or a vegetable and/or pasturization of that juice. Other "processing" operations are well known to those of skill in the art and include, but are not limited to addition of preservatives, exposure to radiation, lyophilization, crystallization, dehydration, comminution, heating (e.g. pasturization), evaporation, lyophylization, filtration, concentration, fermentation, freezing, and blanching.

It was a discovery of this invention that, particularly when screening processed biological samples (preferably processed agricultural products), using labeled lectins, the signal to noise (background) ratio can be dramatically increased by contacting the sample with a pectinase. Indeed, the use of a pectinase, particularly when screening processed plant materials results in an assay that shows a high degree of reliability and sensitivity, and that is commercially viable. Without being bound to a particular theory, it is believed the pectinase degrades one or more components of the sample (e.g. cell wall components) and thereby inhibits and reduces non-specific binding of the lectin to the sample.

Preferred Pectinases.

Essentially any pectinase can be used for this purpose. Pectinases are well known enzymes that characteristically break down pectins (polysaccharides typically found in plant cell walls). The term "pectinases" is intended to include polygalacturonases (EC3.2.1.15), pectinesterases (EC3.2.1.11), pectin lyases (EC4.2.2.10) and hemicellulases such as endo-1,3-β-xylosidase (EC 3.2.1.32), xylan 1,4-β-xylosidase (EC 3.2.1.37), (α-L-arabinofuranosidase (EC 3.2.1.55), and the like. Preferred pectinases include pectic enzymes of fruit or microbial origin, including protopectinases, pectinases, pectinesterase, etc. They also include enzymes used for juice clarification (e.g. clarification pectinase enzymes such as Valley Research Inc.'s , South Bend Ind., USA, Crystlzyme which is obtained from a strain of *Aspergillus niger* var.). A suitable and common source organism for pectinases is *Aspergillus niger*. It is to be understood, however, that any of the enzymes mentioned in the present specification and claims may be produced other organisms, or, alternatively, may be a recombinant enzyme, i.e. a component essentially free of other enzymes or enzyme activity usually occurring in an enzyme product produced by a given microorganism. The recombinant enzyme is typically produced by cloning of a nucleic acid sequence encoding the desired enzyme, transforming a cell to express the enzyme and recovering the enzyme from the cell and/or supernatant in which the cell is cultured. The host cell is preferably a heterologous host, but the host may under certain conditions also be a homologous host.

Pectinases are also commercially available from a number of suppliers. Thus, for example, Enzyme Development Corporation (New York) provides a variety of pectinases (e.g. ENZECO® PECTINASE DV, ENZECO® PECTINASE PX, ENZECO® PECTINASE AJ, etc.) having, inter alia, varying degrees of polygalacturonase and pectin esterase activities. Similarly, Sigma-Aldrich (Milwaukee, Wis., USA) offers a number of pectinases derived from various organisms.

A pectinase such as Valley Research Inc.'s (South Bend Ind. USA) DP 321 (a pectinase "cocktail" of primarily polygalacturonase)is preferably used in a concentration ranging from about 0.1 mL to about 3 mL, preferably 0.3 mL to about 2 mL, more preferably from about 0.5 mL to about 1 mL, and most preferably about 0.5 mL per 3 mL of tomato juice. Preferred concentrations will be similar for other biological samples. It is recognized, however, that the pectinase concentration may be optimized depending on the pectinase utilized and the sample. Such optimization can be routinely accomplished and is facilitated using the ranges provided herein as a starting point. The pectinase can be contacted to the sample prior to application of the lectin, simultaneously with the lectin, or shortly after the lectin has been applied.

Preferred Lectins.

As indicated above, the biological sample is contacted with a lectin "probe" that binds (e.g. that specifically or preferentially binds) chitin or a chitin degradation product. Lectins are sugar-binding proteins that can be derived from many sources including, but not limited to plants, viruses, microorganisms and animals.

between a and b anomers, while others require not only the correct anomeric structure but a specific sequence of sugars for binding.

Figure 5:
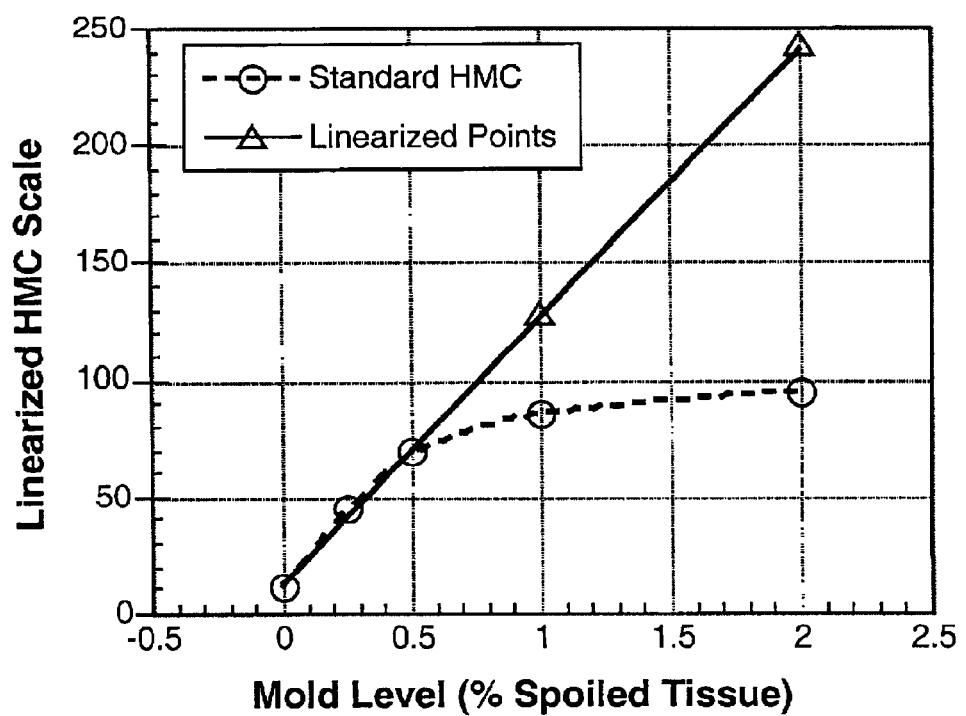
FIG. 5 shows a linearized Howard mold count for tomato juice infected with *Seemphylium botryosum*.

A number of lectins are specific for chitins and/or chitin degradation products. These include, but are not limited to lectins from wheat (Rice and Etzler (1974) *Biochem Biophys Res Comm,* 59: 414–419), barley (Peumans et al. (1982) *Biochem J.* 203: 239–143), rice (Tsuda (1979) *Biochem,* 86:1451–1461), stinging nettle (Peumans et al. (1983) *FEBS Lett,* 177: 99–103), Vicilins from cowpea (*Vigna unguiculata*) and other legume seeds (Sales et al. (1996) *Braz J Med Biol Res, Mar.* 29(3): 319–326), chitovibrin, a lectin secreted by marine bacteria of the genus *Vibrio* (see, e.g., U.S. Pat. No. 5,914,239, and a small protein from the latex of the rubber tree, called hevein (Van Parijs et al. (1991) *Planta,*183: 258–264). To date, all, or most of the chitin-specific lectins contain a conserved cysteine/glycine rich domain (for a review see Raikhel and Broekaert, (1991) In *Control of plant gene expression*, Verma DP (ed), Telford Press). The domain is typically 40–43 amino acids in length and is either repeated twice (nettle lectin), four-fold (in wheat, barley and rice lectins) or fused to an unrelated domain (in basic chitinases and prohevein). Hevein itself is 43 amino acids in length and comprises essentially just this conserved domain (Broekaert et al. (1990) *Proc Nat Acad Sci USA,* 87: 7633–7637). A cDNA clone (HEV1) encoding hevein has been isolated (U.S. Pat. No. 5,187,262. FIG. 5 of WO9411511 shows the common cysteine/glycine-rich domain found in the following Chitin-binding Plant Proteins: tobacco chitinase, bean chitinase, hevein, wheat lectin, nettle lectin. Sequence identities and conserved changes are boxed (conserved changes are considered as substitutions within the amino acid homology groups FWY, MILV, RKH, ED, NQ, ST and PAG; gaps introduced for maximum alignment are represented by dashes). The central region of nine amino acid residues is a particularly well conserved feature of the domain and has the sequence:

```
Cys-Cys-(Ser or Thr)-aa¹-aa²-aa³-(Trp, Tyr, or Phe)-aa⁴-aa⁵-Gly-(Trp, Tyr, or Phe)-aa⁶-aa⁷-
Cys-Gly-aa⁸-aa⁹ (SEQ ID NO: 1, where aa¹–aa⁹ are independently any amino acid).
```

Most lectins are multimeric, consisting of non-covalently associated subunits, however recombinantly expressed lectins are on occasion expressed as single "unit" fusion Around this core region, the central cysteine motif of the cysteine/glycine rich domain is also absolutely conserved and has the sequence:

```
Cys-aa¹-aa²-aa³-aa⁴-Cys-Cys-aa⁵-aa⁶-aa⁷-aa⁸-aa⁹-aa¹⁰-Cys-aa¹¹-aa¹²-aa¹³-aa¹⁴-aa¹⁵-aa¹⁶-Cys
(SEQ ID NO: 2, where aa¹–aa⁹ are independently any amino acid).
``` proteins. A lectin may contain two or more of the same subunit, such as Con A, or different subunits, such as *Phaseolus vulgaris* agglutinin. It is this multimeric structure that typically gives lectins their ability to agglutinate cells or form precipitates with glycoconjugates in a manner similar to antigen-antibody interactions.

Because of the specificity that each lectin has toward a particular carbohydrate structure, even oligosaccharides with identical sugar compositions can be distinguished or separated. Some lectins will bind only to structures with mannose or glucose residues, while others may recognize only galactose residues. Some lectins require that the particular sugar be in a terminal non-reducing position in the oligosaccharide, while others can bind to sugars within the oligosaccharide chain. Some lectins do not discriminate Chitin-specific and/or chitin degradation product specific lectins are also commercially available. Suppliers include, but are not limited to Sigma-Aldrich (Milwaukee, Wis., USA), Vector Laboratories (Burlingame, Calif.), CloneTech (South San Francisco, Calif.) and the like. The lectins are typically available in labeled and/or unlabeled forms.

The lectins when used in this invention are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescent molecules.

A fluorescent label is preferred because it can provide a very strong signal with low background. It is also optically detectable at high resolution and sensitivity through a quick scanning procedure. Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the lectin prior to, or after the lectin is contacted to the sample. So called "direct labels" are detectable labels that are directly attached to or incorporated into the lectin prior application of the lectin to the sample. In contrast, so called "indirect labels" are joined to the bound lectin after it has contacted the sample. Often, the indirect label becomes attached to a binding moiety present on the lectin before it is contacted to the sample. Thus, for example, the lectin may be biotinylated before it is used in the assay. After the lectin is bound to chitinous contaminants in the sample, an avidin-conjugated fluorophore will bind the biotin on the lectin thereby providing a label that is easily detected. Methods of labeling and detecting lectins are similar to those for labeling and detecting antibodies and/or nucleic acids and are well known to those of skill in the art.

The label is attached to the lectin directly or through a linker moiety. In general, the site of label or linker-label attachment is not limited to any specific position on the lectin. Thus, the label may be attached to an amino or carboxyl terminus of the lectin or to the R group of any amino acid(s) comprising the lectin as long as it does not interfere with specific binding of the lectin.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) Science, 281: 2013–2016). Similarly, highly fluorescent quantum dots (zinc sulfide-capped cadmium selenide) have been covalently coupled to biomolecules for use in ultrasensitive biological detection (Warren and Nie (1998) Science, 281: 2016–2018).

The label is detected using a method appropriate to the nature of the label. Thus, for example, enzymatic labels are detected by providing the appropriate substrate and reaction conditions for the enzyme and detecting loss of substrate or increase of reaction product. Radioactive labels are detected, e.g. via scintillography. Fluorescent labels and/or calorimetric labels are detected using optical methods (e.g. fluorometry, image analysis, etc). In a particularly preferred embodiment, the lectin is labeled with a fluorescent label and the label is detected using surface fluorimetry as described below and in Example 2.

The label is attached to the lectin according to any of a number of methods well known to those of skill in the art. Linkage of the lectin to the label can be direct or through a covalent linker. Proteins contain a variety of functional groups; e.g., carboxylic acid (COOH) or free amine (—NH2) groups, which are available for reaction with a suitable functional group on either the surface or on a linker attached to the surface. Proteins, for example, may be joined to linkers or to functional groups on the label by coupling through their amino or carboxyl termini, or through side groups of various constituent amino acids. Thus, coupling through a disulfide linkage to a cysteine is common.

Generally linkers are either hetero- or homo-bifunctional molecules that contain two or more reactive sites that may each form a covalent bond with the respective binding partner (i.e. lectin and label). Linkers suitable for joining such molecules are well known to those of skill in the art. For example, a protein molecule may be linked by any of a variety of linkers including, but not limited to a peptide linker, a straight or branched chain carbon chain linker, or by a heterocyclic carbon linker. Heterobifunctional cross linking reagents such as active esters of N-ethylmaleimide have been widely used. See, for example, Lerner et al. (1981) Proc. Nat. Acad. Sci. (USA), 78: 3403–3407 and Kitagawa et al. (1976) J. Biochem., 79: 233–236, and Birch and Lennox (1995) Chapter 4 in Monoclonal Antibodies: Principles and Applications, Wiley-Liss, N.Y.). In one embodiment, where the label is a polypeptide (e.g. Green Fluorescent Peptide), it can be expressed as a fusion with the lectin.

Detection of Contaminants in Unprocessed ("Raw") Samples.

In still another embodiment, this invention provides methods of detecting contaminants in unprocessed ("raw") samples. These methods typically involve detecting chitinous material in a non-chitinous biological sample, e.g., by comprising contacting the lectin probe with the sample in a solution at a pH ranging from about 7 to about pH 9, and detecting binding of the lectin to a chitin where the binding indicates the presence of chitin in the biological sample. It was a surprising discovery of this invention that performing the lectin assay at a basic pH (e.g. about pH 7 to about pH 9, preferably about pH 7.5 to about pH 8.5, more preferably about pH 8 to pH 8.5, and most preferably about pH 8) provides an assay with a substantially higher signal to noise ratio that other lectin based assays. Without being bound to a particular theory, it is believed the higher pH reduces non-specific binding of the lectin to the non-chitinous sample material. The improvement in signal to noise is so significant that it results in an economical, commercially viable, reliable assay where none was previously present.

It is also noted that performance of the assay at basic pH is not restricted to unprocessed samples. To the contrary, processed samples also benefit when they are run at this pH as well.

The detection of ligand binding in unprocessed samples is also facilitated by the use of a band pass filter when analyzing fluorescent signals as opposed to the long-pass filter typically used in such applications. Again, this is not limited to the analysis of unprocessed samples, and assays of processed samples profit from this approach as well.

In certain preferred embodiments, detection of the labeled lectin involves separation of the lectin from the sample homogenate. This can be accomplished by any of a number of methods. In one preferred approach, the lectin is bound to (incubated with) the sample, and the incubated mixture is then filtered (e.g. with a paper filter, nitrocellulose filter, a nylon filter, derivatized nylon filter, etc.). The filter, which retains lectin bound to contaminant (e.g. mold) is then washed allowing unbound lectin to wash through. The bound lectin is then eluted from the filter (e.g. using chitin, a chitin degradation product, a chitin analog, etc.). In a particularly preferred embodiment, the lectin is eluted using N-acetyl D-glucosamine in Tris-HCL buffer (pH 10). The transparent eluate containing labeled (e.g. fluorescent) lectin is then measured for content of labeled lectin (e.g. using a VICAM fluorometer).

Reading of Signal and Assay Optimization.

As indicated above, the method of detecting the bound lectin depends on the nature of the label. Each type of label (e.g. radioactive, fluorescent, magnetic) has its own characteristic detection technology. Thus, for example, magnetic labels are detected by magnetometers and/or by contacting the magnetic material with a ferrous material and measuring the amount of magnetic material bound to the ferrous material. Enzymatic labels are detected by providing appropriate substrate and reaction conditions and measuring depletion of the substrate or accumulation of the enzymatic reaction product. Radioactive labels are typically detected using scintillography. Colorimetric and fluorometric labels are typically detected visually or by using various optical means.

In a preferred embodiment, the label is a fluorescent label and the label is detected and/or quantified using methods well known for the detection of such labels. Preferred methods include, but are not limited to the use of image-acquisition systems to visualize a sample (e.g. under a microscope) and localize and quantify the associated label and/or the use of fluorometers to detect and/or quantify the label.

While any "general purpose" fluorometer can be used for this purpose, in a preferred embodiment, detection is by use of a "surface reading" (e.g. bottom reading) fluorometer one embodiment of which is illustrated in Example 2. Briefly, this fluorometer utilizes a centrifuge tube comprising a transparent wall. The centrifuge tube is fashioned such that the sample, when spun in a centrifuge, pellets against the transparent wall. The wall (e.g. the bottom of the tube) is then illuminated at the excitation wavelength of the fluorochrome using either a monochrome light source or a broadband source with a narrow band filter. The fluorescence is then measured with a detector, preferably a detector that has a narrow band filter centered at the fluorochrome emission wavelength.

It was a surprising discovery that accurate and reproducible readings with a good signal to noise ratio could be obtained using this method. Moreover, these results could be obtained without the multiple washing steps typically required in such an assay.

In a preferred embodiment, a signal is scored as positive and/or quantified when it can be distinguished above background. In preferred embodiments, the signal is scored when it is significantly above background (e.g. at 90% or greater, more preferably at the 95% or greater, and most preferably at the 98% or 99% or greater confidence level). Most preferred signals are at least 1.2 fold, preferably at least 1.5 fold, more preferably at least 2 fold, and most preferably at least 4 fold above background.

Using the information provided herein, one of ordinary skill can optimize the assays of this invention for particular sample materials (e.g. particular agricultural products) and/or particular lectins, label, and, optionally, processing operations. Optimization is accomplished by running the assay with the desired components and altering pH, and/or label, and/or signal detection system and/or signal analysis algorithm, etc. until the assay shows acceptable level of sensitivity, selectivity, and reproducibility, e.g. as compared to a standard assay. Such a comparison is illustrated in Example 1 for tomato processing.

High Throughput Screening.

The assays of this invention are well suited to a high-throughput screening (HTS) modality. Using automated sample-handling methods, and detection methods, and, optionally, flow through centrifugation devices with associated fluorometers, literally thousands or tens of thousands of samples can be screened in a day. Sample volume can be kept quite low and the cost per assay can be competitive with the best (least expensive) currently existing methods.

High throughput assay systems are well known to those of skill in the art and many such systems are commercially available. (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems typically provide detailed protocols for various high throughput screens.

Kits.

In still another embodiment, this invention provides kits for practice of the methods described herein. In one preferred embodiment, the kits comprise one or more containers containing lectins that specifically bind to chitin or a chitin degradation product. The lectin may be labeled or unlabeled and the kits may, optionally include labels and/or reagents for labeling the lectin and/or for detecting the label. The kits may also, optionally include a centrifugable receptacle suitable for use with a surface-reading fluorometer. The kits may also, optionally include a pectinase.

The kits may optionally include any reagents and/or apparatus to facilitate practice of the methods described herein. Such reagents include, but are not limited to buffers, instrumentation (e.g. bandpass filter), and the like.

In addition, the kits may include instructional materials containing directions (i.e., protocols) for the practice of the methods of this invention. Preferred instructional materials provide protocols utilizing the kit contents for detecting chitinous contaminants in processed or "raw" biological samples. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

A Fluorescent Lectin Test for Contaminants of Agricultural Products

Fungal (mold) contamination is an important indicator of low quality raw product in the processing tomato industry. This example describes the development of a quantitative lectin assay that is less expensive, faster, and more precise than the industry standard Howard mold count. This assay, based on a fluorescent-labeled lectin isolated from wheat germ, had a selective affinity for the chitin in fungal cell walls. Assay values were correlated with mold contamination for four fungal species: *Alternaria alternata* ($r^2=0.91$), *Cladosporium herbarum* ($r^2=0.75$), *Fusarium oxysporum* ($r^2=0.97$), and *Stemphylium botryosum* ($r^2=0.99$). Combining all four species, the lectin assay had a strong correlation ($r^2=0.76$) with a linearized Howard mold count.

Materials and Methods.

Fungal Cultures

Ripe, defect free processing tomatoes (variety Heinz 8892) were washed and surface disinfected for 10 minutes with a 2% sodium hypochlorite solution. Each of four sets of 20 fruit was placed onto a sterile wire mesh in a sterile container. Cultures of *Alternaria alternata, Cladosporium herbarum, Fusarium oxysporum*, and *Stemphylium botryosum*, isolated from tomato fields, were grown on potato dextrose agar at 22° C. for up to 21 days. Each fruit was pricked just below the surface with a sterile knife and inoculated with one of four fungal pathogens. The fruit were placed into an incubator at 26° C. for two to five days (depending upon fungal growth rate) with 16 h of light and 8 h of darkness per day. The fruit remained in the incubator until the fungi spoiled approximately 2% (by mass) of the tomato tissue (FIG. 1).

The spoiled volume (Battilani et al. (1996) *Ital. J. Food Sci.* 4: 283–289) was cut from each fruit in a set and added to unspoiled tissue from additional ripe, defect free processing tomatoes (variety Heinz 8892) and comminuted for 40 s in a blender (Waring model CB-6, Hartford, Conn.) to obtain 3.6 kg of juice containing 2% spoiled tissue (by mass). A separate set of 80 defect-free processing tomatoes were also comminuted for 40 s in the blender to obtain 3.6 kg of juice containing no spoiled tissue. The tomato juice with 2% spoiled tissue and the juice with no spoiled tissue were filtered (640 micron pore size) and combined proportionally to obtain five juice samples with spoiled tissue dilution levels of: 0.0%, 0.25%, 0.5%, 1.0%, and 2.0% (by mass). Each dilution level was subdivided into 40 ml replicate subsamples, placed into sealable tubes, autoclaved at 121° C. for 20 min, and then stored at 8° C. for up to three weeks.

Tomato Tissue Autofluorescence

Clean mold-free juice was diluted and placed into a scanning fluorometer (Hitachi F-2000, San Jose, Calif.). The excitation wavelength was set at 490 nm and the emission spectrum was recorded from 220 nm to 800 nm (5 nm bandwidth). An emission spectrum was also recorded for a FITC labeled WGA lectin solution excited at 490 nm, near its reported excitation maximum.

Fungal Cultures

Ripe, defect free processing tomatoes (variety Heinz 8892) were washed and surface disinfected for 10 minutes with a 2% sodium hypochlorite solution. Each of four sets of 20 fruit was placed onto a sterile wire mesh in a sterile container. Cultures of *Alternaria alternata, Cladosporium herbarum, Fusarium oxysporum*, and *Stemphylium botryosum*, isolated from tomato fields, were grown on potato dextrose agar at 22° C. for up to 21 days. Each fruit was pricked just below the surface with a sterile knife and inoculated with one of four fungal pathogens. The fruit were placed into an incubator at 26° C. for two to five days (depending upon fungal growth rate) with 16 h of light and 8 h of darkness per day. The fruit remained in the incubator until the fungi spoiled approximately 2% (by mass) of the tomato tissue (FIG. 1).

The spoiled volume (Battilani et al. (1996) *Ital. J. Food Sci.* 4: 283–289) was cut from each fruit in a set and added to unspoiled tissue from additional ripe, defect free processing tomatoes (variety Heinz 8892) and comminuted for 40 s in a blender (Waring model CB-6, Hartford, Conn.) to obtain 3.6 kg of juice containing 2% spoiled tissue (by mass). A separate set of 80 defect-free processing tomatoes were also comminuted for 40 s in the blender to obtain 3.6 kg of juice containing no spoiled tissue. The tomato juice with 2% spoiled tissue and the juice with no spoiled tissue were filtered (640 micron pore size) and combined proportionally to obtain five juice samples with spoiled tissue dilution levels of: 0.0%, 0.25%, 0.5%, 1.0%, and 2.0% (by mass). Each dilution level was subdivided into 40 ml replicate subsamples, placed into sealable tubes, autoclaved at 121° C. for 20 min, and then stored at 8° C. for up to three weeks.

Howard Mold Count Procedure

Four tomato processors each received 60 tomato juice samples, consisting of three blind replicates of the five spoiled tissue dilution levels for each of the four fungal species. These processors performed a Howard mold count, viewing two slides for each sample, and the percent of positive fields was recorded.

Fungal Cultures

Ripe, defect free processing tomatoes (variety Heinz 8892) were washed and surface disinfected for 10 minutes with a 2% sodium hypochlorite solution. Each of four sets of 20 fruit was placed onto a sterile wire mesh in a sterile container. Cultures of *Alternaria alternata, Cladosporium herbarum, Fusarium oxysporum*, and *Stemphylium botryosum*, isolated from tomato fields, were grown on potato dextrose agar at 22° C. for up to 21 days. Each fruit was pricked just below the surface with a sterile knife and inoculated with one of four fungal pathogens. The fruit were placed into an incubator at 26° C. for two to five days (depending upon fungal growth rate) with 16 h of light and 8 h of darkness per day. The fruit remained in the incubator until the fungi spoiled approximately 2% (by mass) of the tomato tissue (FIG. 1).

The spoiled volume (Battilani et al. (1996) *Ital. J. Food Sci.* 4: 283–289) was cut from each fruit in a set and added to unspoiled tissue from additional ripe, defect free processing tomatoes (variety Heinz 8892) and comminuted for 40 s in a blender (Waring model CB-6, Hartford, Conn.) to obtain 3.6 kg of juice containing 2% spoiled tissue (by mass). A separate set of 80 defect-free processing tomatoes were also comminuted for 40 s in the blender to obtain 3.6 kg of juice containing no spoiled tissue. The tomato juice with 2% spoiled tissue and the juice with no spoiled tissue were filtered (640 micron pore size) and combined proportionally to obtain five juice samples with spoiled tissue dilution levels of: 0.0%, 0.25%, 0.5%, 1.0%, and 2.0% (by mass).

Each dilution level was subdivided into 40 ml replicate subsamples, placed into sealable tubes, autoclaved at 121° C. for 20 min, and then stored at 8° C. for up to three weeks.

Lectin Assay

Another set of 60 (5 dilution levels×4 species×3 replicates) juice samples was used in the lectin assay. One of the 60 tubes was randomly selected, 10 ml of juice pippetted into a 50 ml centrifuge tube, along with 40 ml of Tris buffer, pH 8.3 (Brooks et al., 1997), centrifuged in a swinging bucket centrifuge (IEC Clinical Model) at 5000 RPM (2260 g) for 1 min, and 40 ml of the supernatant were removed. Highly reactive nonspecific binding sites were blocked with 200 µl of 30% bovine serum albumin (Sigma Chemical, St. Louis, Mo.), and 50 µl of 1 mg/ml FITC labeled WGA lectin (EY Labs, San Mateo, Calif.) was added. The tube was shaken for 40 min in the dark on a wrist action shaker to allow adequate binding to occur. Lectin buffer (40 ml) was added, and the tubes centrifuged at 5000 RPM (2260 g) for 1 min. The supernatant was removed, leaving only the cells pelleted at the bottom. The centrifuging and washing step was repeated once. The washed cells were resuspended in 10 ml of buffer before fluorometer measurement.

A fluorometer (Turner Model 450, Barnstead/Thermolyne, Dubuque, Iowa) was used to quantify the presence of FITC labeled lectin, equipped with a 490 nm excitation bandpass filter (Turner NB490, 10 nm bandwidth) and a 520 nm emission bandpass filter (Turner NB520, 10 nm bandwidth). The 520 nm emission bandpass filter was used to block out the autofluorescent signal at wavelengths longer than the fluorescein emission. The fluorometer was calibrated daily with a standard solution of FITC-labeled WGA lectin. The readings were checked with this solution every thirty minutes during the study, to correct for small levels of instrument drift. Juice from the prepared sample was poured into a 5 ml borosilicate glass circular cuvette (Fisher Scientific, Pittsburgh, Pa.), and a reading recorded on the fluorometer. The cuvette was emptied and rinsed, and the cuvette refilled with sample. A total of five readings were averaged to obtain the fluorescent score for each sample.

The precision of the lectin assay and of the HMC assay were evaluated by calculating the CV across blind replicate measurements conducted on each mold dilution level/species treatment. The usual analysis of variance assumptions of a normal distribution and equal variance across groups were not valid for the coefficient of variance values analyzed. Both the modified Levene (Levene (1960). Robust tests for the equality of variances. In I. Olkin (ed.) *Contributions to probability and statistics*. Stanford University Press; Brown and Forsythe (1974) *Techonometrics* 16: 129–132) and Bartlett (Bartlett and Kendall (1946) *JRSS Suppl.* 8:128–138) tests showed that the variance of coefficient of variation values were significantly ($\alpha=0.01$) different between assays. The Kruskal-Wallis one-way analysis of variance test was used in place of the usual analysis of variance technique because it does not rely on these assumptions.

Fungal Cultures

Ripe, defect free processing tomatoes (variety Heinz 8892) were washed and surface disinfected for 10 minutes with a 2% sodium hypochlorite solution. Each of four sets of 20 fruit was placed onto a sterile wire mesh in a sterile container. Cultures of *Alternaria alternata, Cladosporium herbarum, Fusarium oxysporum,* and *Stemphylium botryosum,* isolated from tomato fields, were grown on potato dextrose agar at 22° C. for up to 21 days. Each fruit was pricked just below the surface with a sterile knife and inoculated with one of four fungal pathogens. The fruit were placed into an incubator at 26° C. for two to five days (depending upon fungal growth rate) with 16 h of light and 8 h of darkness per day. The fruit remained in the incubator until the fungi spoiled approximately 2% (by mass) of the tomato tissue (FIG. 1).

The spoiled volume (Battilani et al. (1996) *Ital. J. Food Sci.* 4: 283–289) was cut from each fruit in a set and added to unspoiled tissue from additional ripe, defect free processing tomatoes (variety Heinz 8892) and comminuted for 40 s in a blender (Waring model CB-6, Hartford, Conn.) to obtain 3.6 kg of juice containing 2% spoiled tissue (by mass). A separate set of 80 defect-free processing tomatoes were also comminuted for 40 s in the blender to obtain 3.6 kg of juice containing no spoiled tissue. The tomato juice with 2% spoiled tissue and the juice with no spoiled tissue were filtered (640 micron pore size) and combined proportionally to obtain five juice samples with spoiled tissue dilution levels of: 0.0%, 0.25%, 0.5%, 1.0%, and 2.0% (by mass). Each dilution level was subdivided into 40 ml replicate subsamples, placed into sealable tubes, autoclaved at 121° C. for 20 min, and then stored at 8° C. for up to three weeks.

Microscopic Observation

Samples from the assay were observed under an epifluorescent microscope (Zeiss, standard model), equipped with a fluorescein filter set (Excitation model BP 490, Emission model LP 520) to check both lectin binding to mold cells and nonspecific binding to tomato tissue.

Results and Discussion.

Tomato Tissue Autofluorescence

Figure 2:
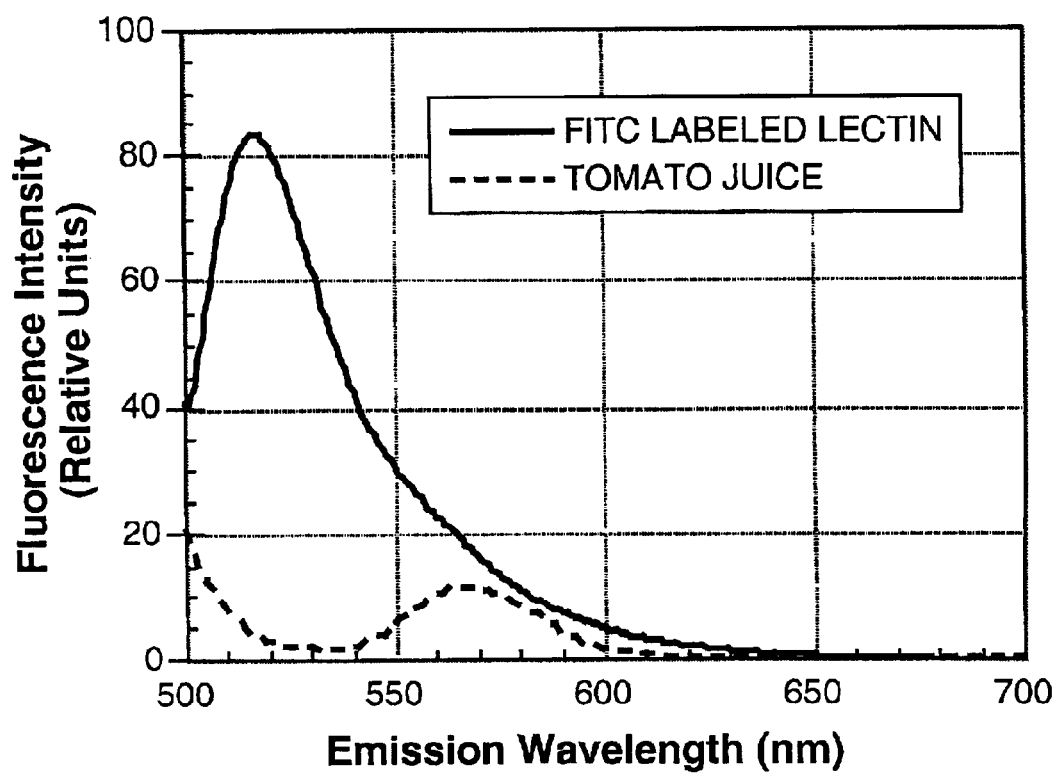
FIG. 2 shows a plot of tomato tissue autofluorescence and FITC labeled WGA lectin emission as a function of emission wavelength for a 490 nm excitation.

The fluorescence emission spectra maximum from fresh tomato juice occurred at a longer wavelength than the maximum for FITC labeled lectin when excited at 490 nm (FIG. 2). Microscopic observations showed that strongest tomato autofluorescence was observed in the fibrovascular bundles, the stem cells, and the skin cells. The wavelength difference between the emission maximum and the excitation maximum is known as the Stokes' shift, and represents the loss of energy due to molecular dissipation. The Stokes' shift for tomato tissue was consistently around 80 nm for excitation in the visible range. Fortunately, FITC, like most commonly used fluorescent labels, has a considerably smaller Stokes' shift of only 15–20 nm. Long-pass filters are normally used in fluorometer emission measurements, so the photomultiplier tube would detect the autofluorescent light. However, we used a bandpass filter, where only a narrow band of light, centered at 520 nm (bandwidth), would be detected by the fluorometer, to eliminate the tomato autofluorescent signal shown in FIG. 2 and also observed by Patel (1992) *Trends in Food Sci. & Technol.* 3: 35–39.

Howard Mold Count Results

The Howard Mold Count scores for the juice samples in this study ranged from 0 to 100% for all mold species except *C. herbarum* which had a maximum HMC of 96%. The average (across all dilution levels) amount of mold for each species was 0.75% spoiled tissue by mass. The average (across all dilution levels) HMC scores for each species however, ranged from a low of 37.4% for *C. herbarum* to a high of 64.2% for *A. alternata*, Table 1.

TABLE 1

Fungal species variability in average HMC levels for tomato juice with an average spoiled tissue mass of 0.75%.

| | Howard Mold Count (%) | |
|---|---|---|
| Species | Mean* | Standard Deviation |
| Alternaria alternata | 64.2a | 18.3 |
| Stemphylium botryosum | 53.1ab | 16.7 |
| Fusarium oxysporum | 46.2bc | 14.9 |
| Cladosporium herbarum | 37.4c | 14.5 |

*Mean values with the same grouping letter are not significantly different ($\alpha = 0.05$).

Figure 3:
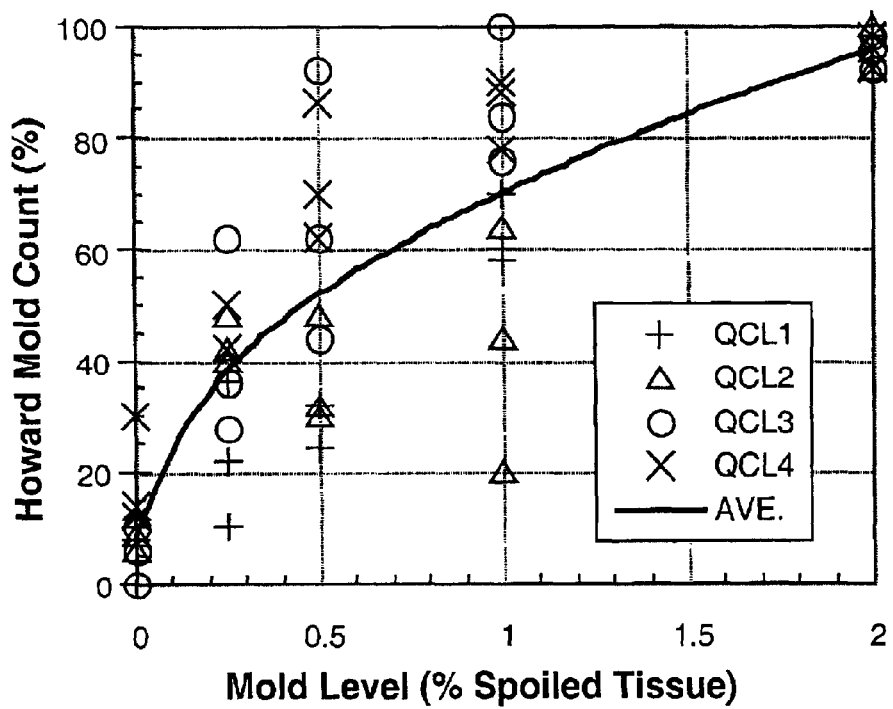
FIG. 3 shows a plot of the Howard mold count results for tomato juice infected with *Stemphylium botryosum*.

The HMC results were nonlinear with spoiled tissue dilution level (FIG. 3) due to field saturation where additional fungal mycelia in an already positive field did not increase the readings. Considerable variability, particularly at the intermediate spoiled tissue levels, was observed between the HMC scores obtained by the different quality control laboratories (QCL). The variability was lower at both the zero and maximum spoiled tissue levels, since no value can be under 0 or over 100% respectively. The overall average coefficient of variation (CV) between the average HMC scores of all four quality control laboratories was 35%. The HMC scores obtained by the quality control laboratories were well correlated, Table 2, with the best agreement occurring between labs 3 and 4 (r=0.97).

TABLE 2

Correlations between average Howard mold count values obtained by four quality control laboratories.

| | QCL1 | QCL2 | QCL3 | QCL4 |
|---|---|---|---|---|
| QCL1 | 1.00 | — | — | — |
| QCL2 | 0.93 | 1.00 | — | — |
| QCL3 | 0.91 | 0.85 | 1.00 | — |
| QCL4 | 0.91 | 0.85 | 0.97 | 1.00 |

Lectin Assay Results

Figure 4:
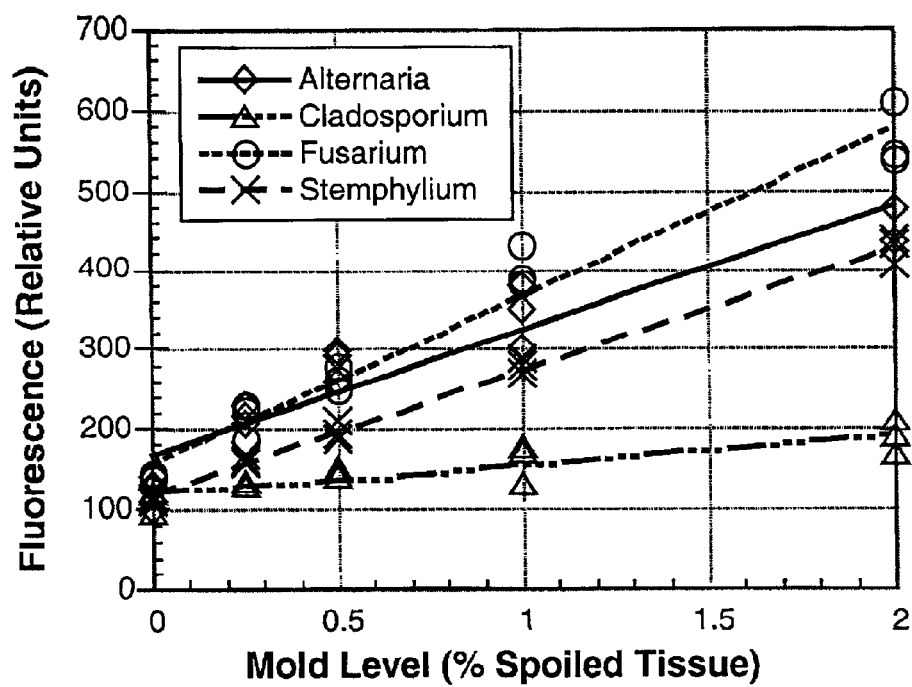
FIG. 4 shows a plot of fluorescence using the lectin assay as a function of mold level.

In contrast to the HMC assay, the lectin assay results were linear with spoiled tissue dilution level resulting in the following coefficients of determination: A. alternata $r^2=0.91$, C. herbarum $r^2=0.75$, F. oxysporum $r^2=0.97$, S. botryosum $r^2=0.99$, all species combined $r^2=0.59$, FIG. 4. This linearity is important, both because, unlike HMC, it allows the lectin scores to directly indicate actual mold levels making them easier to compare and because it makes calibration simpler. The nonlinear HMC method was at saturation at 2% spoiled tissue for three of the four species. A Kruskal-Wallis one-way analysis of variance test showed that the precision of the lectin assay was significantly better (($\alpha$=0.02)) than the precision of the IMC assay performed by any of the quality control laboratories, Table 3.

TABLE 3

Average coefficient of variation (CV) values for HMC and WGA lectin mold assay.

| Evaluator | Ave. CV* |
|---|---|
| QCL1 | 50.3%a |
| QCL2 | 45.6%a |
| QCL3 | 42.0%a |
| QCL4 | 21.6%b |
| WGA Lectin Assay | 7.2%c |

*CV values with the same grouping letter are not significantly ($\alpha = 0.02$) different.

Although the spoiled volume dilution will give accurate relative results (i.e. 0.5% level has exactly one quarter the mold as 2% level), it is unlikely that there is the same dry weight of mold mass in the original 2% mold levels for different fungal species. For example, the average HMC at 0.5% spoiled tissue dilution was 94 for A. alternata and 40 for C. herbarum. Since the HMC gives an indication of fungal biomass, we used these scores to adjust for varying amounts of fungal biomass in the undiluted contaminated juice. Because the HMC is by nature non-linear with high variability, we developed a linearized HMC score to compare with the lectin assay. The HMC scores of the two quality control laboratories (3 and 4) which had the best precision among blind replicate measurements and the highest correlation between laboratories were averaged and used as the "true" Howard mold count for mold levels in the study. Four mold levels for C. Herbarum (i.e. 0% through 1% spoiled tissue) and three mold levels for the remaining fungal species (i.e. 0% through 0.5% spoiled tissue) were regressed against the spoiled volume to develop linearized HMC models for each species. These models were then used to predict linearized HMC scores above the linear range for each species.

Figure 6:
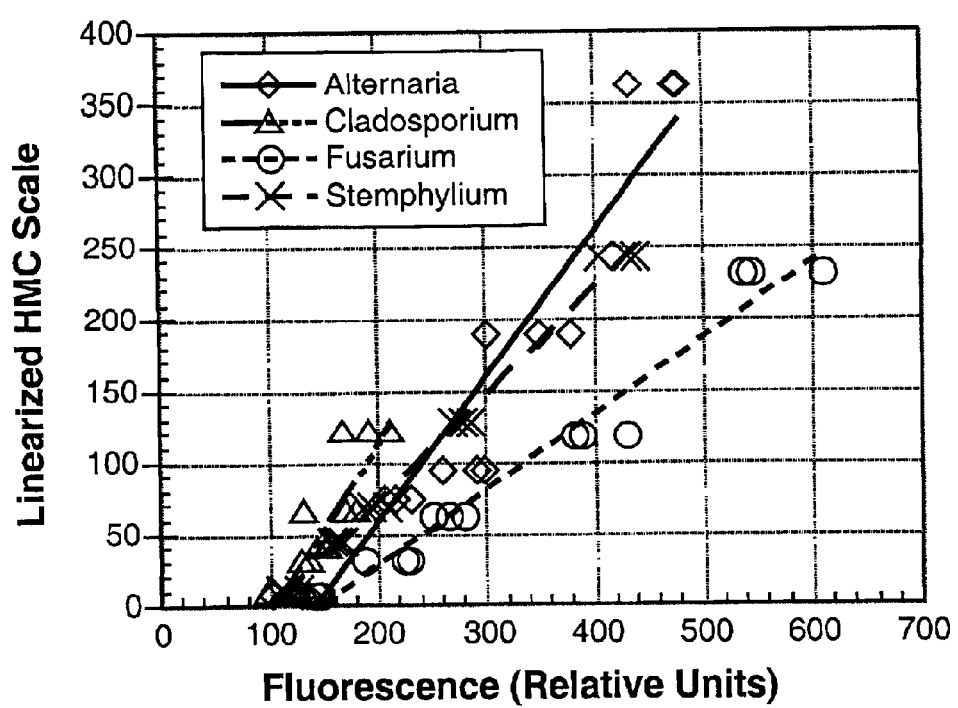
FIG. 6 shows a plot of the lectin assay versus a linearized Howard mold count for tomato juice infected with *Stemphylium botryosum*.

FIG. 5. The linearized HMC scores were then regressed against the lectin assay readings resulting in the following coefficients of determination: A. alternata $r^2=0.91$, C. herbarum $r^2=0.76$, F. oxysporum $r^2=0.97$, S. botryosum $r^2=0.99$, all species combined $r^2=0.76$, FIG. 6. These results show that the lectin assay will give generally comparable results to HMC in the linear range for each fungal organism. Differences in response among species are either intrinsic in the lectin assay (i.e. species differ in amounts of chitin, or in number of exposed chitin-binding sites, Sharma et al. (1977) Trans. Br. Mycol. Soc. 69: 479–483; Cousin (1996) Journal of Food Protection, 59: 73–81), may reflect that species differ in ratio of fungal mass to spoiled tissue mass, or HMC scores may differ for similar quantities of different mold species, Table 1. Eisenburg (1952) Nat. Can. Assoc., Inf Let. No. 1371 observed high levels of variability among fungal species when comparing the relationship between HMC and spoiled volume in individual tomatoes. Battilani et al. (1996) Ital. J. Food Sci. 4: 283–289, also observed fungal species variability in both the relationship between HMC and spoiled volume as well as the relationship between HMC and ergosterol content.

The lectin assay required 120 min for a group of 12 samples, or an average of 10 min per sample. This is one-third the time required for an accurate HMC analysis. The total cost of reagents used in the lectin assay were $0.60 US. The cost of the lectin assay in a commercial application could be reduced further if the reagents were purchased in large quantities.

Microscope Observations

WGA lectin bound strongly to the mycelia of all four species. Strongest binding occurred at the hyphal tips and in the septa (cross-walls), although there was generally an adequate coating of older wall surfaces. It did not, however, bind the asexual conidia of any of the species, with the exception of F. oxysporum, which exhibited some lectin binding to macroconidia.

Conclusion.

This example describes the development of a rapid and inexpensive test for mold (or other chitinous contaminants) which can replace the Howard mold count for testing of mold or other chitinous contaminants) in a wide variety of biological samples (e.g. raw tomato juice). The test is linear, with 3 to 7 times better precision than the Howard mold count for the fungal species tested. Lectins are inexpensive and the assay takes around 10 min per sample when analyzed in groups of 12, one-third the time required for an effective official Howard mold count. With binding time reductions, it has the potential to be a much faster assay, and can be automated. Correlations with mold count results suggest there is an acceptably low variation across the fungal species tested (Alternaria alternata, Cladosporium herbarum, Fusarium oxysporum, and Stemphylium botryosum).

Example 2

Figure 7:
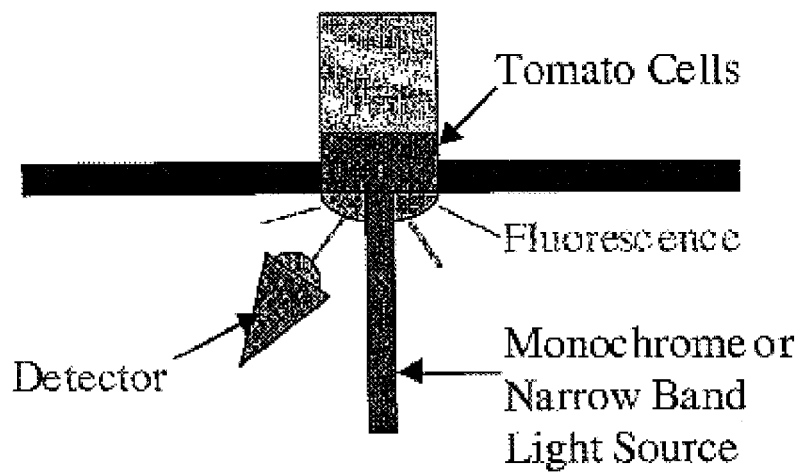
FIG. 7 shows an illustration of a surface reading fluorometer. Solid or semi-solid material 10 (e.g. tomato cells) in the of the two-phase solution 18 (sample) is deposited against a transparent surface/window 12. A light source 14 illuminates the sample through the window 12 thereby exciting the fluorophore on the bound lectin. The resulting fluorescence is detected by the detector 16. Phase two 20 of the two phase solution is shown as well. The surface/window can be a part of a centrifugable receptacle (e.g. a centrifuge tube).

Surface Fluorometry for Detection of a Fluorochrome Bound to One Phase of a Two-Phase Mixture FIG. 7 shows an illustration of a surface reading fluorometer. Solid or semi-solid material 10 (e.g. tomato cells) in the sample is deposited against a transparent surface/window 12. A light source 14 illuminates the sample through the window 12 thereby exciting the fluorophore on the bound lectin. The resulting fluorescence is detected by the detector 16. The surface/window can be a part of a centrifugable receptacle (e.g. a centrifuge tube).

Normally, the unbound reagent (labeled lectin) must be removed in a washing step that requires two centrifuge steps. In one embodiment, in place of the standard conically bottomed centrifuge tube we are using a centrifuge tube with a flat clear (i.e., transparent) bottom. In this single centrifuge process, the biological sample (e.g. tomato cells) gets pelleted at the bottom of the tube while the remaining "serum" and other soluble materials and some unbound lectin in solution end up on top. The bottom of the tube is then illuminated at the excitation wavelength of the fluorochrome using either a monochrome light source or a broadband source with a narrow band filter. In a preferred embodiment, the fluorescence is then measured with a detector that has a narrow band filter centered at the fluorochrome emission wavelength.

Figure 8:
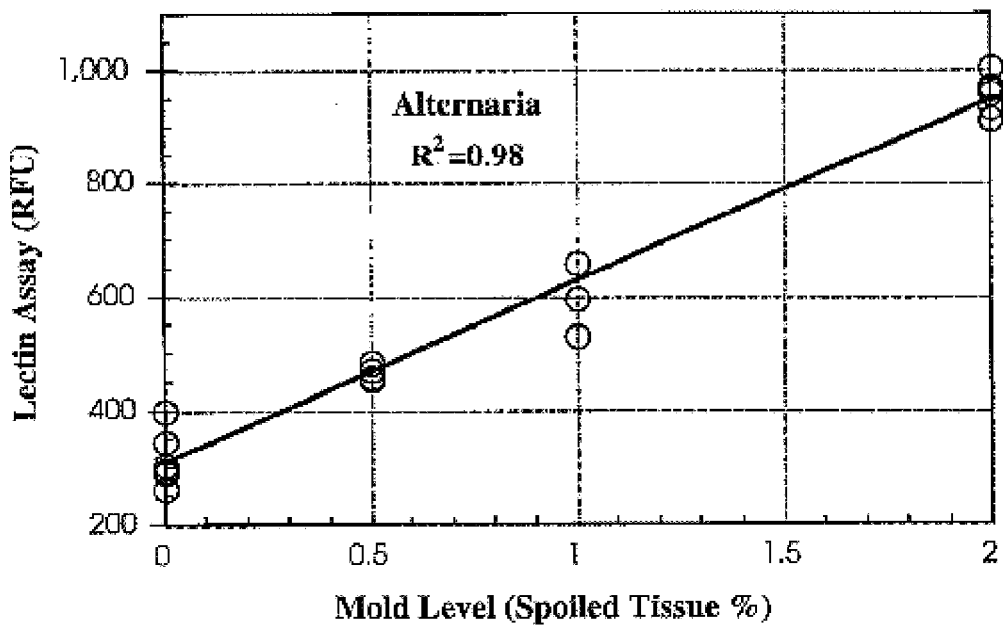
FIG. 8 shows results from a lectin assay results using a surface-reading fluorometer.

As a proof of concept, we disassembled a Turner fluorometer and rearranged the optics into a standard 0-degree excitation angle and 45-degree detection angle geometry shown below (other standard reflectance geometries could be used as well). The remaining components of the fluorometer were unchanged. We then tested the prototype using a dilution series with various levels of Altemaria infected tomato juice. The results of that test are shown in FIG. 8.

Example 3

Preparation and Analysis of Tomato Juice for Mold Contamination Level

This experiment aimed to establish a standard curve describing the correlation between level of mold contamination and VICAM fluorescence units. Tomato juice with different levels of mold contamination (0, 0.5, 1, 2, 3, 4, 5, 6, 7, and 8%) was prepared. The assay range was determined according to recommendations of the Processing Tomato Advisory Board (PTAB) for samples contaminated between 0% and 8% by weight with moldy fruit.

Preparation of Tomato Juice with 8% Mold Contamination by Weight

The following rational was followed: For a given amount (Xg) of non-contaminated (fresh) fruit, the amount (Yg) of mold-contaminated fruits to be added to the Xg to obtain tomato juice with 8% mold contamination was: Yg=(Xg*0.08)/0.92. The mold-contaminated fruit was obtained by inoculating fresh fruit, previously rinsed thoroughly, with mold (*Altenaria alternata*) and incubating at room temperature for 6 days. The spoiled part of the contaminated tomato fruit was cut away, weighed, and mixed with fresh tomato fruit to make 8%, by weight, of mold-contaminated mixture. This combined mix was then ground for 60 seconds at high speed in a laboratory blender (Waring, New Haven, Conn.). The resulting extract was filtered through a strainer to remove fruit seeds, giving a heavy tomato juice kept in a refrigerator for further use. Serial dilutions (0, 0.1, 1, 2,3, 4, 5, 6, 7) from the 8% mold contamination by weight was made by combining 8% and 0% (fresh) tomato juice to create the desired percentage of mold. For each dilution level, 5 ml was used for the assay and 10 identical aliquots per dilution level were prepared.

Lectin binding.

Twenty (20) $\mu$M of fluorescent wheat germ agglutinin (WGA) lectin conjugate (Molecular Probes, Eugene, Oreg.) in TRIS-HCL buffer pH 10 was used as the binding solution. Ten (10) mL of the lectin solution was added to each 5 mL juice aliquot. The mixture was incubated for 5 min at room temperature, allowing the lectin to bind to mold chitin contained in the moldy tomato juice.

Unbound Lectin Separation.

The incubated mixture was filtered. The filter, which retains lectin bound to mold, was washed twice with 20 mL water allowing unbound lectin to wash through the filter.

Elution and Mold Count.

Ten (10) mL of N-acetyl D-glucosamine (Aldrich Chemical Corp., Milwaukee Wis.) (250 mM) in TRIS-HCL buffer, pH 10, was used as a eluent to release bound lectin from the filter. The collected transparent eluate, containing fluorescent lectin was measured for content of fluorescent material by using a VICAM fluorometer previously calibrated with Tomato Mold test standard.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting chitinous material in a processed non-chitinous biological sample, said method comprising
   contacting said biological sample with a probe that is a lectin that binds chitin;
   contacting said biological sample with a pectinase;
   filtering said sample;
   washing said filter to remove unbound lectin;
   eluting bound lectin with a chitin, a chitin degradation product or a chitin analogue; and
   detecting said lectin wherein detection of said lectin indicates the presence of chitinous material in said biological sample.

2. The method of claim 1, wherein said chitin comprises an insect, an insect part, or any animal of the phylum Arthropoda subphylum Crustacea.

3. The method of claim 1, wherein said chitin is a component of a microorganism.

4. The method of claim 3, wherein said microorganism is selected from the group consisting of a fungus, a mold, and a yeast.

5. The method of claim 3, wherein said microorganism is a selected from the group consisting of a fungus of phylum Ascomycota, a fungus of phylum Basidomycota, a fungus of phylum Chytridiomycota, a fungus of phylum Zygomycota, and a member of the phylum Oomycota in the Stramenopila kingdom.

6. The method of claim 3, wherein said microorganism is a fungus selected from the group consisting of Cladosporium spp, Fusarium spp, Stemphylium spp, Alternaria spp, Geotrichurn spp, Rhizopus spp, Botrytis spp, Phytophthora spp, and Pythium spp.

7. The method of claim 1, wherein said biological sample is a selected from the group consisting of an agricultural product, a food product, a wood product, a textile, and an animal tissue product.

8. The method of claim 7, wherein said agricultural product is selected from the group consisting of a fruit, a vegetable, a grain, forage, a silage, a juice, a wood, a flower, and a seed.

9. The method of claim 7, wherein said agricultural product is a fruit selected from the group consisting of a tomato, a pepper, a grape, an apple, an orange, a lemon, and a berry.

10. The method of claim 1, wherein said lectin is selected from the group consisting of wheat germ agglutinin (WGA), succinylated WGA, pokeweed lectin, tomato lectin, potato lectin, barley lectin, rice lectin, stinging nettle lectin, a vicilin, a chitovibrin, a Vibrio lectin, and a hevein.

11. The method of claim 1, wherein said method further comprises contacting said sample with a blocking reagent.

12. The method of claim 11, method wherein said blocking reagent is serum albumin.

13. The method of claim 1, wherein said chitin degradation product is N-acetyl D-glucosamine.

14. The method of claim 1, wherein said lectin is labeled with a detectable label.

15. The method of claim 14, wherein said label is selected from the group consisting of a radioactive label, a magnetic label, a colorimetric label, an enzymatic label, a fluorescent label, a metal, an antibody, a biotin, and an avidin or streptavidin.

16. The method of claim 14, wherein said label is a fluorescent label.

17. The method of claim 16, wherein said detecting comprises using a fluorometer to detect fluorescence of said label.

18. The method of claim 17, wherein said fluorometer uses a bandpass filter.

19. The method of claim 17, wherein said fluorometer is a surface-reading fluorometer.

20. The method of claim 17, wherein said fluorometer is a surface-reading fluorometer.

21. The method of claim 16, wherein said detecting comprises using a fluorometer to detect fluorescence of said label.

22. The method of claim 14, wherein said label is selected from the group consisting of a radioactive label, a magnetic label, a colorimetric label, an enzymatic label, a fluorescent label, a metal, an antibody, a biotin, and an avidin or streptavidin.

23. The method of claim 14, wherein said label is a fluorescent label.

24. The method of claim 1, wherein said method is performed at a pH greater than about pH 7.

25. The method of claim 1, wherein said method is performed at about pH 8.

26. The method of claim 1, wherein said pectinase comprises an enzyme selected from the group consisting of polygalacturonases, pectinesterases, pectin lyases, and hemicellulases.

27. The method of claim 1, wherein the processed biological sample is a sample that has been subjected to an operation selected from the group consisting of comminuting, homogenizing, heating, evaporation, lyophilization, filtering, concentrating, fermenting, freezing, and blanching.

28. The method of claim 1, wherein
the biological sample is selected from the group consisting of a fruit, a vegetable, a fruit juice, and a vegetable juice;
said lectin is a fluorescently labeled lectin selected from the group consisting of wheat germ agglutinin (WGA), succinylated WGA, pokeweed lectin, tomato lectin, potato lectin, barley lectin, rice lectin, stinging nettle lectin, a vicilin, a chitovibrin, a Vibrio lectin, and a hevein;
said pectinase is a pectinase selected from the group consisting of polygalacturonases, pectinesterases, pectin lyases and hemicellulases;
said sample is processed by an operation selected from the group consisting of comminuting, homogenizing, heating, evaporation, lyophilization, filtering, concentrating, fermenting, freezing, and blanching; and
said detecting comprises detecting a signal from the fluorescent label labeling said lectin.

29. A method of detecting chitinous material in a non-chitinous biological sample, said method comprising
in a solution at a pH ranging from about pH 7 to about pH 9 contacting said biological sample with a fluorescently labeled probe that is a lectin that binds chitin;
filtering said sample;
washing said filter to remove unbound lectin;
eluting bound lectin with a chitin, a chitin degradation product or a chitin analogue; and
detecting said lectin wherein detection of said lectin indicates the presence of chitinous material in said biological sample.

30. The method of claim 29, wherein said chitin comprises an insect or insect part.

31. The method of claim 29, wherein said chitin is a component of a microorganism.

32. The method of claim 31, wherein said microorganism is selected from the group consisting of a fungus, a mold, and a yeast.

33. The method of claim 31, wherein said microorganism is a fungus selected from the group consisting of *Cladosporium herbarum, Fusarium oxysporum,* and *Stemphyliuin botryosum, Altemaria alternata, Geotrichum candidum, Rhizopus stolonifer, Botrytis cinerea, Phytophthora parasitica, Pythium aphanidermatum, Pythium ultimum.*

34. The method of claim 29, wherein said biological sample is selected from the group consisting of an agricultural product, a food product, a wood product, a textile, and an animal tissue product.

35. The method of claim 34, wherein said agricultural product is selected from the group consisting of consisting of a fruit, a vegetable, a grain, forage, a silage, a juice, a wood, a flower, and a seed.

36. The method of claim 34, wherein said agricultural product is a fruit selected from the group consisting a fruit, a vegetable, a grain, forage, a silage, a juice, a wood, a flower, and a seed.

37. The method of claim 29, wherein said lectin is selected from the group consisting of wheat germ agglutinin (WGA), succinylated WGA, pokeweed lectin, tomato lectin, potato lectin, barley lectin, rice lectin, stinging nettle lectin, a vicilin, a chitovibrin, a Vibrio lectin, and a hevein.

38. The method of claim 29, wherein said method further comprises contacting aid sample with a blocking reagent.

39. The method of claim 38, wherein said blocking reagent is serum albumin.

40. The method of claim 29, wherein said chitin degradation product is N-acetyl D-glucosamine.

41. The method of claim 29, wherein said lectin is labeled with a detectable label.

42. The method of claim 29, wherein said method is performed at a basic pH greater than about pH 7.5.

43. The method of claim 29, wherein said method is performed at a basic pH about pH 8.0.

44. The method of claim 29, wherein
the biological sample is selected from the group consisting of a fruit, a vegetable, a fruit juice, and a vegetable juice; said lectin is a fluorescently labeled lectin selected from the group consisting of wheat germ agglutinin (WGA), succinylated WGA, pokeweed lectin, tomato lectin, potato lectin, barley lectin, rice lectin, stinging nettle lectin, a vicilin, a chitovibrin, a Vibrio lectin, and a hevein; and
said detecting comprises detecting a signal from the fluorescent label labeling said lectin.

45. The method of claim 29, further comprising contacting said biological sample with a pectinase.

46. The method of claim 45, wherein said pectinase is selected from the group consisting of polygalacturonases, pectinesterases, pectin lyases and hemicellulases.

* * * * *

UNITED STATES PATENT AND TRADEMARK OFFICE
CERTIFICATE OF CORRECTION

PATENT NO. : 6,833,250 B2  Page 1 of 1
DATED : December 21, 2004
INVENTOR(S) : Barb Ariel Cohen It is certified that error appears in the above-identified patent and that said Letters Patent is hereby corrected as shown below:

<u>Title page,</u>
Item [75], Inventors, should read -- Barb Ariel Cohen, Watertown, MA (US) --

<u>Column 24,</u>
Line 17, delete "*Stemphyliuin*" and replace with -- *Stemphylium* --.
Line 18, delete "*Altemaria*" and replace with -- *Alternaria* --.

Signed and Sealed this

Nineteenth Day of July, 2005

JON W. DUDAS
*Director of the United States Patent and Trademark Office*